(12) United States Patent
Sansone et al.

(10) Patent No.: US 8,754,093 B2
(45) Date of Patent: Jun. 17, 2014

(54) CO-CRYSTAL OF ETRAVIRINE AND NICOTINAMIDE

(75) Inventors: Matthew F. Sansone, Lexington, MA (US); Mark Tawa, Acton, MA (US); Julius F. Remenar, Framingham, MA (US); Lieven Elvire Colette Baert, Bruges (BE)

(73) Assignee: Janssen R&D Ireland, Little Island, Co, Cork (IE)

( * ) Notice: Subject to any disclaimer, the term of this patent is extended or adjusted under 35 U.S.C. 154(b) by 270 days.

(21) Appl. No.: 13/262,077

(22) PCT Filed: Mar. 26, 2010

(86) PCT No.: PCT/EP2010/053970
§ 371 (c)(1),
(2), (4) Date: Sep. 29, 2011

(87) PCT Pub. No.: WO2010/112411
PCT Pub. Date: Oct. 7, 2010

(65) Prior Publication Data
US 2012/0028998 A1    Feb. 2, 2012

Related U.S. Application Data

(60) Provisional application No. 61/164,516, filed on Mar. 30, 2009.

(51) Int. Cl.
*C07D 239/46* (2006.01)
*A61K 31/455* (2006.01)

(52) U.S. Cl.
USPC ............................................. 514/272; 544/321

(58) Field of Classification Search
USPC ............................................. 544/321; 514/272
See application file for complete search history.

(56) References Cited

FOREIGN PATENT DOCUMENTS

| WO | WO 00/27825 A1 | 5/2000 |
|---|---|---|
| WO | WO 01/22938 A1 | 4/2001 |
| WO | WO 01/23362 A2 | 4/2001 |
| WO | WO 03/089414 A1 | 10/2003 |
| WO | WO 2008/068299 A2 | 6/2008 |
| WO | WO 2008/109785 A2 | 9/2008 |
| WO | WO 2009/011567 A1 | 1/2009 |

OTHER PUBLICATIONS

International Search report for Application No. PCT/EP2010/053970 mailed Aug. 3, 2010.

*Primary Examiner* — Deepak Rao
(74) *Attorney, Agent, or Firm* — Michael J. Atkins (57) ABSTRACT

Etravirine (TMC125) nicotinamide co-crystal, its preparation, and use in the treatment of HIV infection.

22 Claims, 7 Drawing Sheets

A view of a molecule of TMC125:nicotinamide co-crystal from the crystal structure showing the numbering scheme employed. Anisotropic atomic displacement ellipsoids for the non-hydrogen atoms are shown at the 50% probability level. Hydrogen atoms are displayed with an arbitrarily small radius.

FIG. 5

A view of the molecular packing for TMC125:nicotinamide co-crystal from the crystal structure.

FIG. 6

Plot of the primary hydrogen bonding interactions of TMC125:nicotinamide co-crystal observed in the crystal structure of TMC125:nicotinamide.

FIG. 7

CO-CRYSTAL OF ETRAVIRINE AND NICOTINAMIDE

CROSS REFERENCE TO RELATED APPLICATIONS

This application is a national stage of PCT Application No. PCT/EP2010/053970, filed Mar. 26, 2010, which claims priority from U.S. Provisional Application Ser. No. 61/164,516, filed Mar. 30, 2009, all of which are hereby incorporated by reference in their entirety.

This invention concerns a co-crystal of etravirine (TMC125) and nicotinamide, its preparation and use in the treatment of HIV infection.

BACKGROUND OF THE INVENTION

The treatment of Human Immunodeficiency Virus (HIV) infection, generally recognized as cause of the acquired immunodeficiency syndrome (AIDS), remains a major medical challenge. Currently available HIV inhibitors include nucleoside reverse transcriptase inhibitors (NRTIs), non-nucleoside reverse transcriptase inhibitors (NNRTIs), nucleotide reverse transcriptase inhibitors (NtRTIs), HIV-protease inhibitors (PIs), fusion inhibitors, and the more recent CCR5 and integrase inhibitors.

Current standard of care is based on combination therapy of several anti-HIV agents of a different activity profile. One class of HIV drugs used in combinations is that of the NNRTIs, a number of which are currently on the market while others are in various stages of development. An NNRTI that is on the market is the compound 4-[[6-amino-5-bromo-2-[(4-cyanophenyl)amino]-4-pyrimidinyl]oxy]-3,5-dimethylbenzonitrile, also referred to as etravirine or as TMC125. In a growing number of countries, etravirine is on the market under the tradename "Intelence™". This compound not only shows pronounced activity against wild type HIV, but also against many mutated HIV strains. Etravirine, its pharmacological activity, as well as a number of procedures for its preparation have been described in WO 00/27825.

Etravirine is very insoluble in aqueous media and therefore suffers from very low bioavailability. Traditional formulations resulted in no or very low blood plasma levels. WO 01/23362 and WO 01/22938 disclose solid dispersions of this compound in water-soluble polymers offering improved bioavailability, especially when in the form of powders prepared by spray-drying. Intelence™ is available as tablets that contain a solid dispersion of TMC125 in HPMC obtained by spray-drying. The current dosing regimen of etravirine is 200 mg twice a day (b.i.d.), administered as two tablets each containing 100 mg, to be taken in at once, preferably two in the morning and two at the end of the day. Because of these dosing requirements and the fact that etravirine is dispersed in a relatively large quantity of water-soluble polymer, dosage forms of this drug inevitably are large in size. This contributes to the so-called "pill-burden", a term that covers all inconveniences associated with the intake of drugs such as, for example, frequent daily dosing, specific administration requirements, e.g. before, during or after a meal, large dosage forms, or combinations of these factors. Large dosage forms can be problematic for patients having difficulty in swallowing, such as children or the elderly. Frequent dosing and specific administration requirements put a heavy burden on patients not to forget taking their medication and to take it at the right time. All these factors contribute to the risk that patients will not take their entire dose, thereby failing to comply with the prescribed dosage regimen. As well as reducing the effectiveness of the treatment, this may also lead to the virus becoming resistant to the drug that is administered. The problems associated with a high pill burden are multiplied where a patient must take a combination of a number of different types of pharmaceutical agents such as in anti-HIV therapy.

One way to improve the bioavailability of poorly soluble active agents is by converting them into the amorphous form. Typically, the higher the degree of crystallinity of the pharmaceutical agent, the lower is its bioavailability. Amorphous forms, however, are difficult to prepare and quickly convert to the thermodynamically more stable crystalline form. They can be stabilized by incorporation in a solid dispersion matrix, which in the case of pharmaceuticals typically is a water-soluble polymer. This results in large volume dosage forms since a relatively large amount of matrix material is required to obtain a stable solid dispersion The crystalline state of drug substances is preferred because of the relative ease of isolation, the removal of impurities during the crystallization process, and the physicochemical stability that the crystalline solid state generally affords. These advantages are often counter-balanced by disadvantageous features of the crystalline state, such as poor solubility, hygroscopicity, dissolution rate, and other associated performance characteristics.

The provision of drug substances in co-crystalline forms can offer an alternative approach to modify or control the physicochemical properties of a drug substance. It can offer an alternative to the conversion into the amorphous state with its associated problems or to the conversion into salt forms, which in a number of instances do not offer the desired physicochemical properties. Co-crystallization can also be used to isolate or purify a drug substance during manufacturing.

Pharmaceutical co-crystals are crystalline molecular complexes that contain the drug substance along with an additional molecule present in the same crystal structure. The additional molecule or guest has been described in the literature as a co-crystal former. A co-crystal can thus be seen to be a multiple component crystal in which the drug substance and the co-crystal former are arranged in a three dimensional repetitive structure, wherein non-covalent and non-ion pair interactions exist between the drug substance and the co-crystal former, such as hydrogen bonding, pi-stacking, and van der Waals interactions. Co-crystalline forms show different physicochemical properties compared to the drug substance alone, including melting point, chemical reactivity, apparent solubility, dissolution rate, optical and mechanical properties, vapor pressure, and density. These properties can have a direct effect on the ability to process and/or manufacture a drug substance and the corresponding finalized dosage forms, as well as an effect on drug product stability, dissolution, and bioavailability. Thus co-crystallization can affect the quality, safety, and efficacy of a drug substance.

Co-crystal formation and the properties of co-crystalline forms cannot be predicted on the basis of known properties of the drug substance and the co-crystal former.

Co-crystalline forms of a drug substance can be characterized by a number of methods including, for example, X-ray powder diffraction, microscopy, thermal analysis (e.g. differential scanning calorimetry, thermal gravimetric analysis and hot-stage microscopy), spectroscopy (e.g., infrared (IR) and near infrared (NIR), Raman, solid-state nuclear magnetic resonance (ssNMR)), and in particular by single crystal X-ray diffraction.

It now has been found that etravirine and nicotinamide form a co-crystal that demonstrates improved properties as compared to etravirine alone. This co-crystal shows an improved dissolution profile of etravirine in in-vitro experiments. In particular the dissolution rate in aqueous media (simulated gastric fluid) of the etravirine active ingredient from a solid dispersion is increased and prolonged, resulting in higher concentrations of the drug. This may result into higher plasma levels and a quicker onset of the etravirine active ingredient. This allows for more compact dosage forms, which in turn helps to overcome problems associated with pill burden.

DESCRIPTION OF THE INVENTION

The present invention concerns a co-crystal of etravirine with nicotinamide as well as its preparation or manufacture. The said co-crystal is characterized by its physicochemical parameters, for example those presented hereinafter in the experimental section. The co-crystal exists in a 1:1 (molar) ratio.

The co-crystal of the present invention can be used in the formulation and development of drug products that provide advantageous properties compared to art-known etravirine-based products. These drug products are different from the current, marketed, form of etravirine because the active ingredient is present in a lower energy, crystalline form that has desirable intrinsic properties. The co-crystal has better flow properties, is easier to prepare, shows better physical stability, and has a dissolution profile comparable to the current amorphous drug product.

The invention also concerns a process for preparing the etravirine/nicotinamide co-crystal. In this process etravirine and nicotinamide are dissolved in a solvent, if desired by warming the mixture to complete dissolution. Both ingredients may be dissolved in the same solvent, either together or separately, or separately in a different solvent. In case of separate dissolution of both ingredients, the two solutions are mixed. Solvents that can be used comprise of halogenated hydrocarbons, e.g. chloroform, or dipolar aprotic solvents, e.g. DMF or DMA. The precipitation of the co-crystal occurs upon cooling a solution of etravirine and nicotinamide, for example a solution at higher temperatures, which is allowed to cool to room temperature and, if desired, allowing evaporation of the solvent, such as by introducing a stream of inert gas. In one embodiment, etravirine is dissolved in a solvent whereupon nicotinamide is added. The whole is warmed, for example to about 60° C., until complete dissolution is observed. The solution is allowed to cool back to room temperature as the co-crystal precipitates. Solvent removal via evaporation can be done to increase yield. The co-crystal that is formed can be filtered off and optionally washed and dried.

In still another aspect, there is provided a pharmaceutical formulation comprising one or more etravirine/nicotinamide co-crystals and a carrier, which carrier may comprise one or more pharmaceutically acceptable excipients. The one or more etravirine/nicotinamide co-crystals are present in an anti-HIV effective amount, which is as specified hereinafter. The excipients include surfactants, solubilizers, disintegrants such as microcrystalline cellulose, starch, sodium starch glycolate, and crosslinked carboxy methyl cellulose sodium, crosslinked PVP, pigments, flavors, fillers, lubricants, glidants, preservatives, thickening agents, buffering agents, and pH modifiers. Typical surfactants include sodium lauryl sulfate, Cremophor RH 40™, Vitamin E TPGS and polysorbates, such as Tween 20™. Typical pH modifiers are acids, such as citric acid or succinic acid, bases, or buffers. The formulation in particular is in solid form, but may also be in the form of a dispersion. The pharmaceutical formulation preferably is converted into a solid unitary dosage form such as a tablet, capsule, sachet, pill, powder packet, suppository, and the like. The said pharmaceutical formulation may contain from about 30% to about 90%, or from about 50% to about 80%, or from about 60% to about 75% of etravirine/nicotinamide co-crystals and from about 70% to about 10%, or from about 50% to about 20%, or from about 40% to about 25% of the carrier, wherein each percentage is weight/weight (w/w).

In a further aspect, the invention concerns the etravirine/nicotinamide co-crystal or co-crystals in accordance with the invention for use as a medicine, in particular as a medicine for treating HIV infection or conditions associated with HIV infection. Or alternatively, the invention concerns the use of the etravirine/nicotinamide co-crystal or co-crystals in accordance with the invention for the manufacture of a medicament for inhibiting HIV, or for treating patients infected with HIV. In still a further aspect, there is provided a method of suppressing HIV in a patient infected with HIV, or a method of treating a patient infected with HIV or suffering from conditions associated with HIV infection, said methods comprising the administration of an anti-HIV effective amount of etravirine/nicotinamide co-crystal or co-crystals. An anti-HIV effective amount in this context refers to that amount that results in a reduction of viral load.

The term "anti HIV effective amount" refers to an amount of etravirine that result in a reduction of the viral load of HIV (represented as the number of copies of viral RNA in a specified volume of serum), or increases CD4 count, or both. Preferably the viral load should be reduced to as low levels as possible, e.g. below about 200 copies/ml, in particular below about 100 copies/ml, more in particular below 50 copies/ml, if possible below the detection limit of the virus. Reductions of viral load of one, two or even three orders of magnitude (e.g. a reduction in the order of about 10 to about $10^2$, or more, such as about $10^3$) are an indication of the effectiveness of the treatment. Another parameter to measure effectiveness of anti-HIV treatment is the CD4 count, which in normal adults ranges from 500 to 1500 cells per µl. Lowered CD4 counts are an indication of HIV infection and once below about 200 cells per AIDS may develop. An increase of CD4 count, e.g. with about 50, 100, 200 or more cells per µl, is also an indication of the effectiveness of anti-HIV treatment. The CD4 count in particular should be increased to a level above about 200 cells per µl, or above about 350 cells per µl. Viral load or CD4 count, or both, can be used to diagnose the degree of HIV infection.

Conditions associated with HIV infection include the influenza or mononucleosis-like illness called acute HIV infection, which occurs at the initial stage of infection, the most common symptoms of which may include fever, lymphadenopathy, pharyngitis, rash, myalgia, malaise, mouth and esophagal sores, and may also include, but less commonly, headache, nausea and vomiting, enlarged liver/spleen, weight loss, thrush, and neurological symptoms. When $CD4^+$ T cell numbers decline below a critical level of 200 cells per µL, cell-mediated immunity is lost, and infections with a variety of opportunistic microbes appear. The first symptoms often include moderate and unexplained weight loss, recurring respiratory tract infections (such as sinusitis, bronchitis, otitis media, pharyngitis), prostatitis, skin rashes, and oral ulcerations. Typically, resistance is lost early on to oral *Candida* species and to *Mycobacterium tuberculosis*, which leads to an increased susceptibility to oral candidiasis (thrush) and tuberculosis. Later, reactivation of latent herpes viruses may cause worsening recurrences of herpes simplex eruptions, shingles, Epstein-Barr virus-induced B-cell lymphomas, or Kaposi's sarcoma. Pneumonia caused by the fungus *Pneumocystis jirovecii* is common and often fatal. In the final stages of AIDS, infection with cytomegalovirus (another herpes virus) or *Mycobacterium avium* complex is more prominent.

The co-crystal or co-crystals in accordance with the present invention can be administered in a daily amount that is in the range of about 250 mg to about 900 mg, or of about 350 mg to about 700 mg, or of about 450 mg to about 550 mg, in particular about 500 mg, e.g. 512 mg, each amount referring to the amount of the co-crystal or co-crystals of etravirine/nicotinamide. These quantities can be administered once daily or, which is preferred, twice daily.

It has been found that the dissolution (or solvation) profile of etravirine can be improved when certain ingredients are added to the etravirine/nicotinamide co-crystal or co-crystals of the invention. These dissolution improving ingredients are selected from hydroxypropyl methylcellulose (HPMC), hydroxypropylmethylcellulose phthalate (HPMCP), polyvinylpyrrolidone (PVP), a copolymer of vinylpyrrolidone and vinyl acetate (PVPcoVA), and nicotinamide, including mixtures thereof. Thus in a further aspect, the present invention concerns a pharmaceutical combination comprising one or more etravirine/nicotinamide co-crystals in accordance with the invention and one or more of the above mentioned dissolution improving ingredients. In one embodiment, the weight/weight (w/w) ratio between the one or more etravirine/nicotinamide co-crystals and the said dissolution improving ingredients in these combinations is in the range from about 4:1 to about 1:2, or from about 2:1 to about 1:2. In a particular embodiment said ratio is about 1:1. The said combinations may contain from about 75% to about 25%, or from about 66% to about 33%, or about 50% of etravirine/nicotinamide co-crystal or co-crystals, and from about 75% to about 25%, or from about 66% to about 33%, or about 50% of the one or more dissolution improving ingredients, wherein each percentage is weight/weight (w/w).

The HPMC for use in the combinations described above or in the compositions derived therefrom, preferably contains sufficient hydroxypropyl and methoxy groups to render it water-soluble. HPMC having a methoxy degree of substitution from about 0.8 to about 2.5 and a hydroxypropyl molar substitution from about 0.05 to about 3.0 are generally water-soluble. The methoxy degree of substitution refers to the average number of methyl ether groups present per anhydroglucose unit of the cellulose molecule. The hydroxypropyl molar substitution refers to the average number of moles of propylene oxide which have reacted with each anhydroglucose unit of the cellulose molecule. Hydroxypropyl methylcellulose is the United States Adopted Name for hypromellose. Types of HPMC that can be used in the combinations of the invention are hypromellose 2910 or hypromellose 2208. In the four digit number "2910" or "2208", the first two digits represent the approximate percentage of methoxy groups and the third and fourth digits the approximate percentage of hydroxypropoxyl groups. The HPMC may have an apparent viscosity of about 1 to about 100 mPa·s, of about 1 to about 50 mPa·s, of about 3 to about 20 mPa·s, of about 3 to about 15 mPa·s, when in a 2% (w/v) aqueous solution at 20° C. Preferred HPMCs include hypromellose 2910 5 mPa·s and hypromellose 2910 15 mPa·s. 15 mPa·s (or 15 Cps) or 5 mPa·s (or 5 Cps) is a value indicative of the apparent viscosity of a 2% aqueous solution of the polymer at 20° C. Commercially available grades of HPMC that can be used include hypromellose 2910 E3 (2% viscosity from 2.4 to 3.6 mPa·s), hypromellose 2910 E5 (2% viscosity from 4 to 6 mPa·s), hypromellose 2910 E6 (2% viscosity from 5 to 7 mPa·s), and hypromellose 2910 E15 (2% viscosity from 12 to 18 mPa·s). These grades are available from e.g. Dow Chemicals under the tradename Methocel™. Hypromellose 2208 with the same apparent viscosities can also be used.

Polyvinylpyrrolidines (PVPs) that may be used are known as povidones and are commercially available under the tradename Kollidon™. They may have a molecular weight that is in the range of about 30 kD to about 360 kD. Examples are PVP K12 (BASF, MW 2000-3000), PVP K17 (BASF, MW=7000-11000), PVP K25 (BASF, MW=28000-34000), PVP K29-32, PVP K30 (BASF, MW=44000-54000), and PVP K90 (BASF, MW=1,000,000-1,500,000).

Copolymers of vinylpyrrolidone and vinyl acetate that may be used include those copolymers wherein the molecular ratio of the monomers vinylpyrrolidone to vinyl acetate is about 1.2 or wherein the mass ratio of the monomers vinylpyrrolidone to vinyl acetate is about 3:2. Such copolymers are commercially available and are known as copovidone or copolyvidone, also referred to as PVPcoVA (for example PVPco VA 64), sold under trademarks Kolima™ or Kollidon (e.g. Kollidon VA 64™). The average molecular weight of these polymers may be in the range of about 45 to about 70 kD. The K-value, which relates to the average molecular weight, may be in the range of about 25 to about 35, in particular the K value may be about 28.

Hydroxypropyl methylcellulose phthalate (HPMCP), also referred to as hypromellose acetate, is a cellulose that contains methyl, hydroxypropyl, and phthalyl groups on its cellulose backbone. They usually have a hydroxypropyl content of from 5 to 10%, a methoxy content of from 18 to 24%, and a phthalyl content from 21 to 35%, with average molecular weights in the range 20,000-200,000, in particular 80,000-130,000. Several different types of hypromellose phthalate are commercially available such as for example the products having a hydroxypropyl content of from 6-10%, a methoxy content of from 20-24%, a phthalyl content of from 21-27%, a molecular weight of about 84,000 daltons known under the trade mark HP50 and having a hydroxypropyl content, a methoxyl content, and a phthalyl content of 5-9%, 18-22% and 27-35% respectively, and a molecular weight of 78,000 daltons, known under the trademark HP55, both available from Shin-Etsu Chemical Co. Ltd., Tokyo, Japan. Still another type is HP-55S with a similar hydroxypropyl, methoxy, and phthalyl content as HP55, but with higher viscosity.

One embodiment concerns a combination comprising one or more etravirine/nicotinamide co-crystals in accordance with the invention and hydroxypropyl methylcellulose (HPMC). The HPMC in particular is HPMC 2910 E5 mPa·s or HPMC 2910 E15 mPa·s. Another embodiment concerns a combination comprising one or more etravirine/nicotinamide co-crystals and PVP; or a combination comprising one or more etravirine/nicotinamide co-crystals and PVP and HPMC; or a combination comprising one or more etravirine/nicotinamide co-crystals, PVP and nicotinamide; or a combination comprising one or more etravirine/nicotinamide co-crystals and nicotinamide; or a combination comprising one or more etravirine/nicotinamide co-crystals, nicotinamide and one, two or three ingredients selected from PVP, HPMC, and PVPcoVA, wherein these ingredients may be any of the specific ingredients mentioned herein such as e.g. HPMC 2910 E5 or E15. The w/w ratio of the one or more co-crystals to the dissolution improving ingredient or ingredients can as specified above and e.g. is about 1:1. Examples of combinations are, for example, one or more etravirine/nicotinamide co-crystals and an ingredient selected from HPMC, PVP, and nicotinamide, in particular in a ratio of about 1:1; or one or more etravirine/nicotinamide co-crystals and HPMC, in particular HPMC E5 mPa·s or HPMC E15 mPa·s, in a ratio of about 1:1; or one or more etravirine/nicotinamide co-crystals and PVP, in a ratio of about 1:1; or one or more etravirine/nicotinamide co-crystals, PVP, and HPMC, in particular in a ratio of about 1:1:½, or in a ratio of about 1:2:1; or one or more etravirine/nicotinamide co-crystals, nicotinamide, PVP, and HPMC, in particular in a ratio of about 1:1:1:½.

The combinations of the invention may be administered as such, without further excipients. They can be filled into a capsule, for example a hard gelatin or a HPMC capsule.

In a further aspect, the invention provides a pharmaceutical composition comprising a combination as defined herein and a carrier, which carrier may comprise one or more of the pharmaceutically acceptable excipients mentioned above. In one embodiment, said pharmaceutical composition comprises from about 30% to about 90%, or from about 50% to about 80%, or from about 60% to about 75% of the said combination and from about 70% to about 10%, or from about 50% to about 20%, or from about 40% to about 25% of the carrier, wherein each percentage is weight/weight (w/w). Preferred are solid compositions. These compositions are preferably converted into solid unit dosage forms such as tablets or capsules, e.g. hard gelatin or HPMC capsules.

The compositions of the present invention are more compact and easier to prepare than the currently commercialized formulation of etravirine, which is a spray-dried solid dispersion of etravirine and HPMC in a 1:3 w/w ratio. The presence of HPMC has as consequence that for practical reasons the required 200 mg dose cannot be formulated into one dosage form, rather it is formulated as a 100 mg dosage form, thereby necessitating the intake of two tablets. The co-crystal or co-crystals of this invention can be worked into a 200 mg dosage form that is of acceptable size.

As used herein, the term "about" in connection with a numerical value is meant to have its usual meaning in the context of the numerical value. Where necessary the word "about" may be replaced by the numerical value ±10%, or ±5%, or ±2%, or ±1%.

All documents cited herein are incorporated by reference in their entirety. The singular includes the plural and vice versa, the plural includes the singular. For example, the term "co-crystal" includes "co-crystals", and the term "co-crystals" includes "co-crystal".

EXAMPLES

Example 1

Preparation of TMC125. Nicotinamide Co-Crystal

The free base of TMC125 (10.0 g) was dissolved with nicotinamide (3.0 g) in chloroform (900 mL). This mixture was gently heated at 60° C. for 1 minute to dissolve the remaining solid. Once complete dissolution was observed, the solution was allowed to cool back to room temperature during which the co-crystal precipitated from solution. Once equilibrated at room temperature, $N_2$ gas was gently blown into the flask to reduce the volume of the solution to 100 ml. The product was collected by vacuum filtration at room temperature and allowed to dry.

Example 2

Characterization of TMC125. Nicotinamide Co-Crystal $C_{26}H_{21}BrN_8O_2$

Figure 1:
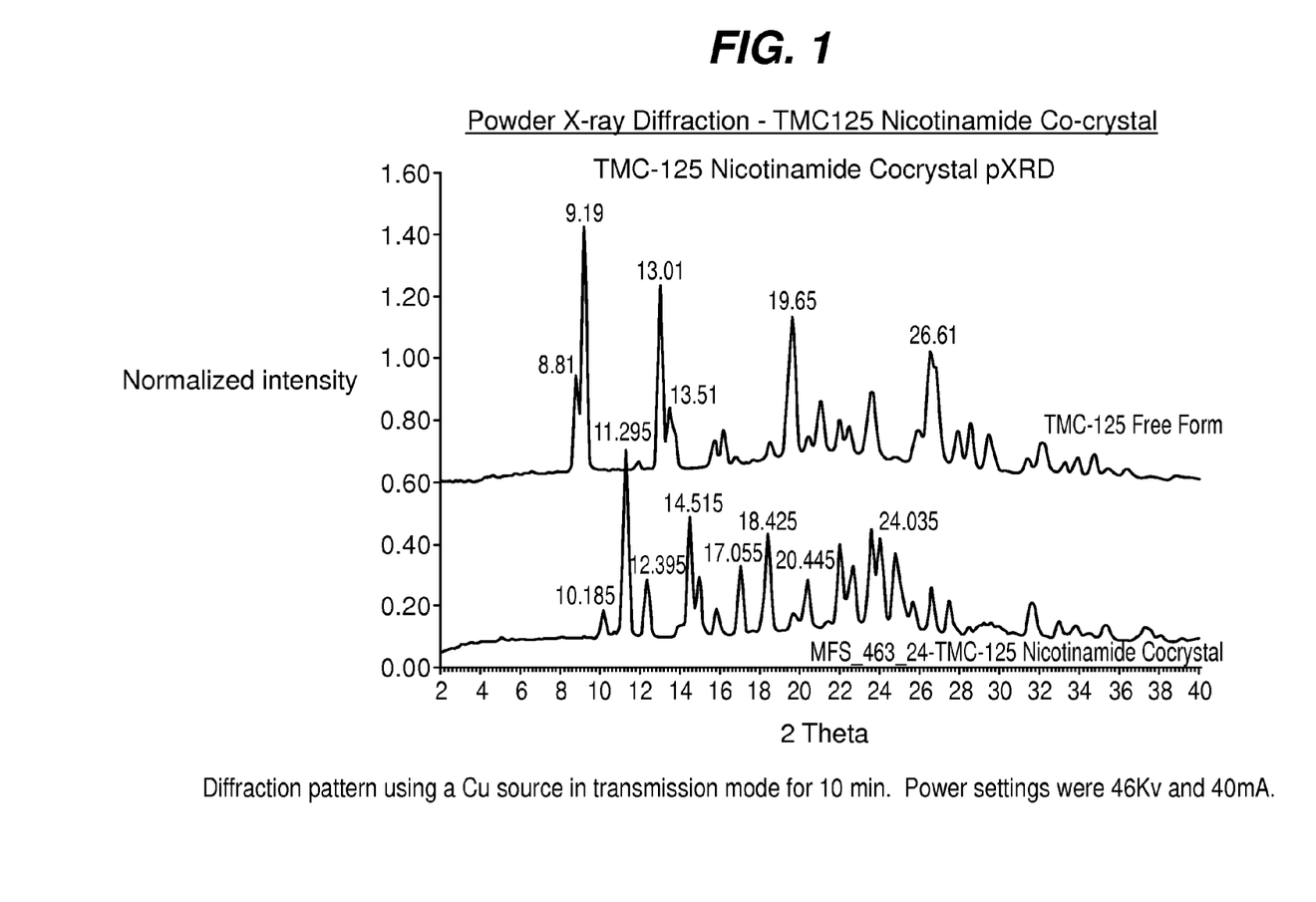
FIG. 1 shows a Powder X-ray Diffraction pattern for the TMC125:nicotinamide co-crystal of Example 2.

The PXRD pattern has characteristic peaks as shown in FIG. 1. Peaks can be seen at 2-theta angles. Characterizing peaks are those located at the following 2-theta angles: 10.19, 11.30, 12.40, 14.52, 17.06, 18.43, 20.45, 24.04.

Figure 2:
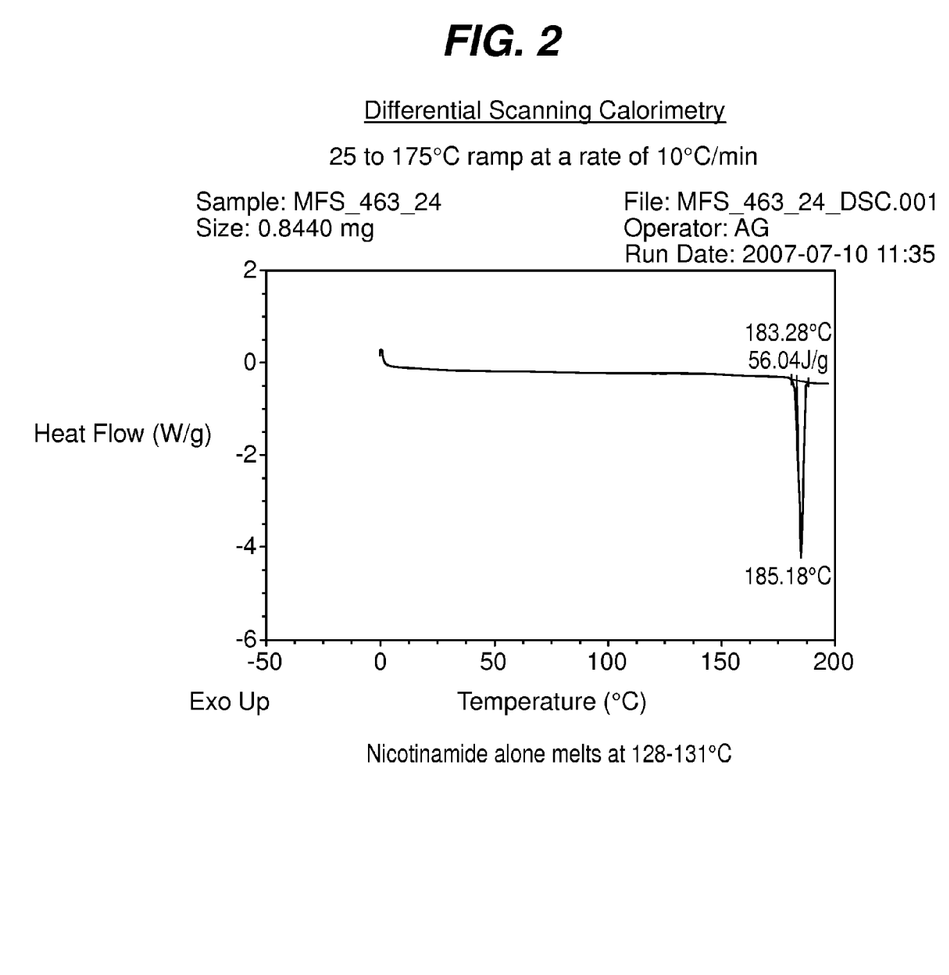
FIG. 2 shows results of DSC analysis for the TMC125:nicotinamide co-crystal of Example 2.
Figure 3:
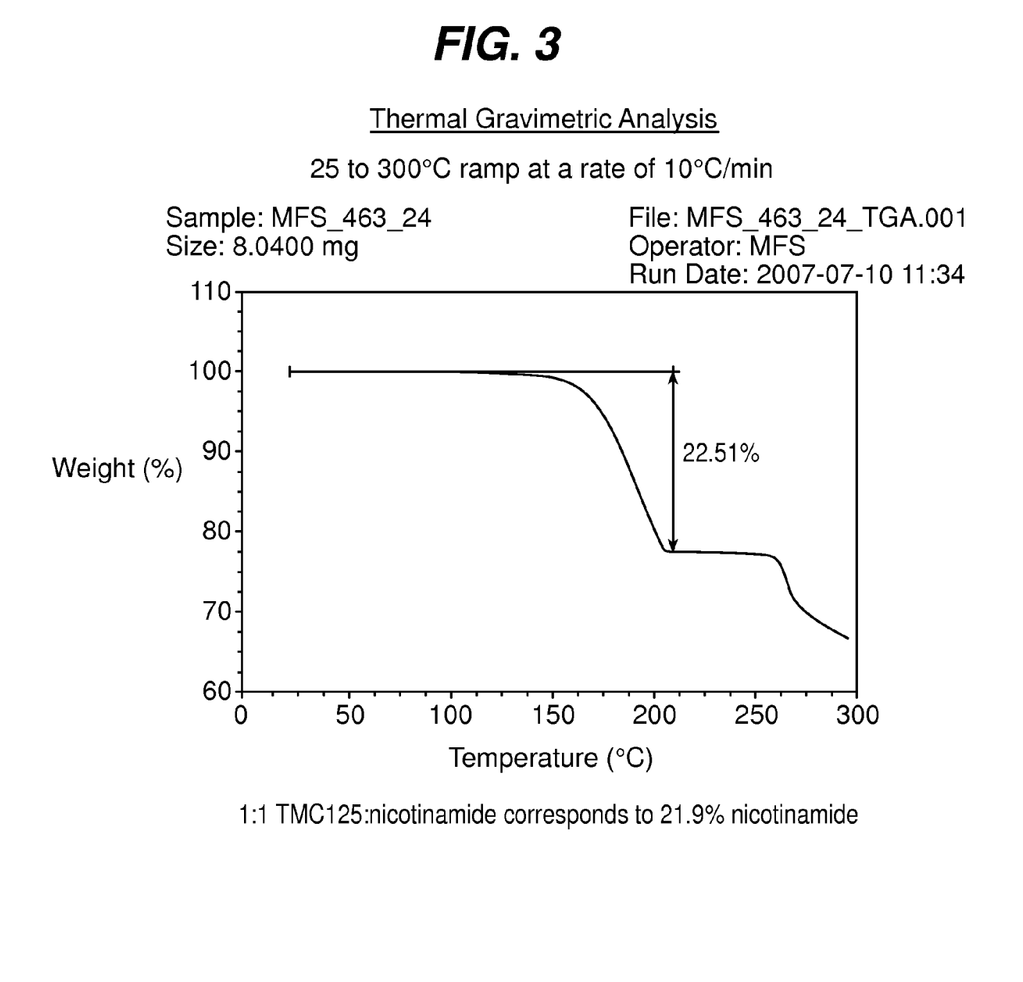
FIG. 3 shows results of TGA analysis for the TMC125:nicotinamide co-crystal of Example 2.
Figure 6:
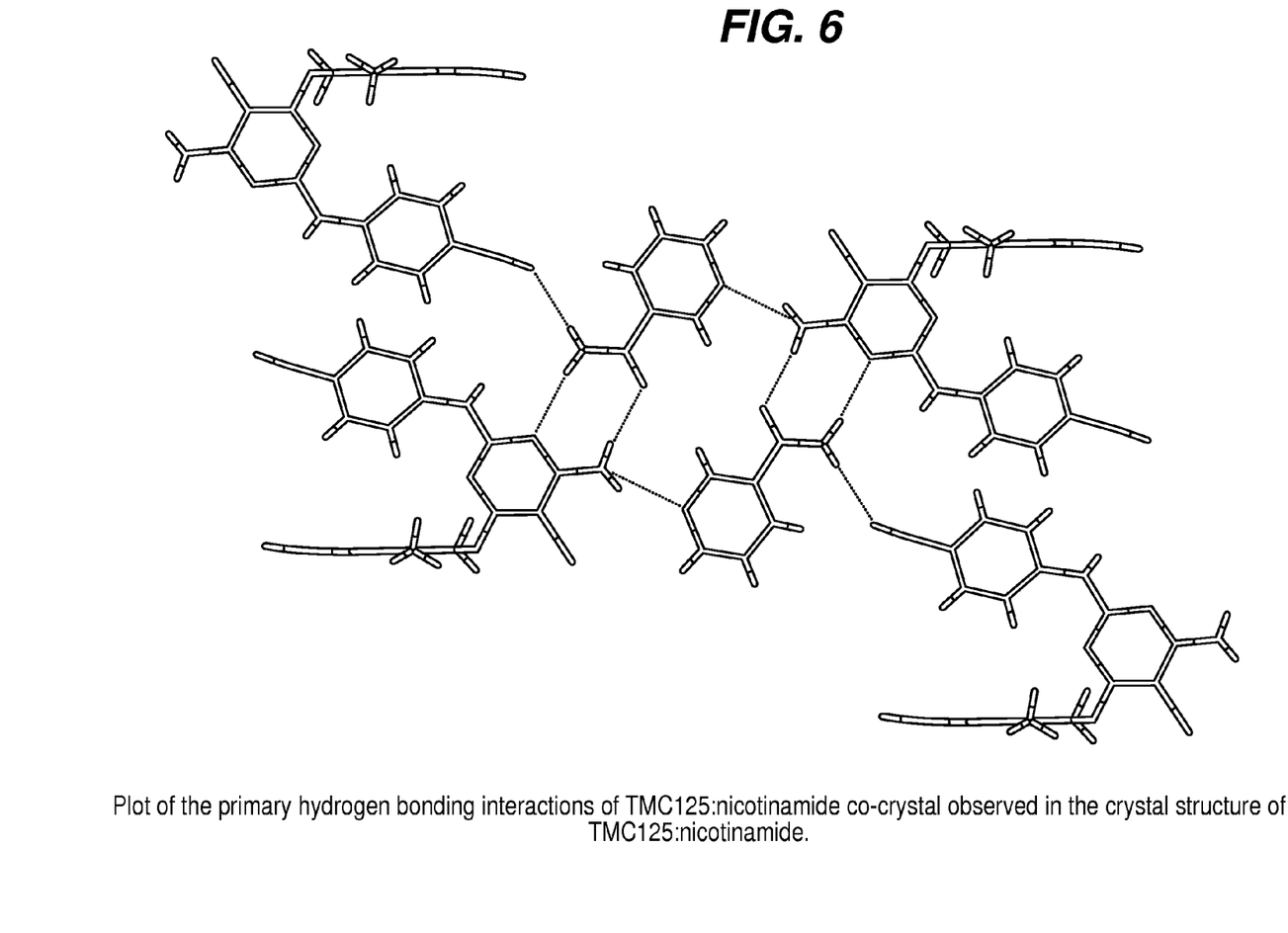
FIG. 6 shows a plot of the primary hydrogen bonding interactions of TMC125:nicotinamide co-crystal observed in the crystal structure.

Results of DSC analysis are shown in FIG. 2. For this analysis, 0.844 mg of collected sample was placed into an aluminum DSC crimp pan with cover. During heating, 50 ml/min nitrogen purge gas was used. Results of the DSC thermogram (FIG. 6) show an endothermic event at 185.18° C., corresponding to a melting of the sample. Results of TGA analysis are also shown in FIG. 6. For this analysis, 8.040 mg of collected sample was placed into a platinum TGA pan. Results of the TGA (FIG. 3) demonstrated a 22.50% weight loss beginning at 100° C. to 210° C. This corresponds to one molar equivalent of nicotinamide melting and escaping from the sample.

A clear plate of $C_{26}H_{21}BrN_8O_2$, approximate dimensions 0.09 mm×0.21 mm×0.38 mm, was used for the X-ray crystallographic analysis. The X-ray intensity data were measured at 100(2) K on a Bruker KAPPA APEX-II CCD™ area detector system equipped with a graphite monochromator and a MoKα fine-focus sealed tube (λ=0.71073 Å) operated at 1.5 kW power (50 kV, 30 mA). The detector was placed at a distance of 4.0 cm from the crystal.

A total of 1384 frames were collected with a scan width of 0.5° in ω and φ and an exposure time of 20 sec/frame. The total data collection time was 8 hours. The frames were integrated with the Bruker SAINT™ software package using a narrow-frame integration algorithm. The integration of the data using a Monoclinic cell yielded a total of 40173 reflections to a maximum θ angle of 36.89° (0.594 Å resolution), of which 11331 were independent (redundancy 3.50), completeness=88.0%, $R_{int}$=3.56%, $R_{sig}$=4.66%) and 8328 (73.5%) were greater than >2 sigma (I) σ ($F^2$). The final cell constants of a=8.1720(4) Å, b=9.0125(4) Å, c=34.7072(14) Å, α=90°, β=94.918(3)°, γ=90°, volume=2546.8(2) Å$^3$, are based upon the refinement of the XYZ-centroids of 7161 reflections above 20 σ(I) with 4.712°<2θ<71.207°. Analysis of the data showed negligible decay during data collection. Data were corrected for absorption effects using the multiscan technique (SADABS). The ratio of minimum to maximum apparent transmission was 0.663. The calculated minimum and maximum transmission coefficients (based on crystal size) were 0.5721 and 0.8627.

The structure was solved and refined using the Bruker SHELXTL™ (Version 6.1) Software Package, using the space group P2(1)/c, with Z=4 for the formula unit, $C_{26}H_{21}BrN_8O_2$. The final anisotropic full-matrix least-squares refinement on $F^2$ with 418 variables converged at R1=4.84%, for the observed data and wR2=10.70% for all data. The goodness-of-fit was 1.053. The largest peak on the final difference electron density synthesis was 1.283 e−/Å$^3$ and the largest hole was −1.407 e−/Å$^3$ with an RMS deviation of 0.085 e−/Å$^3$. On the basis of the final model, the calculated density was 1.454 g/cm$^3$ and F(000), 1136 e−.

Figure 4:
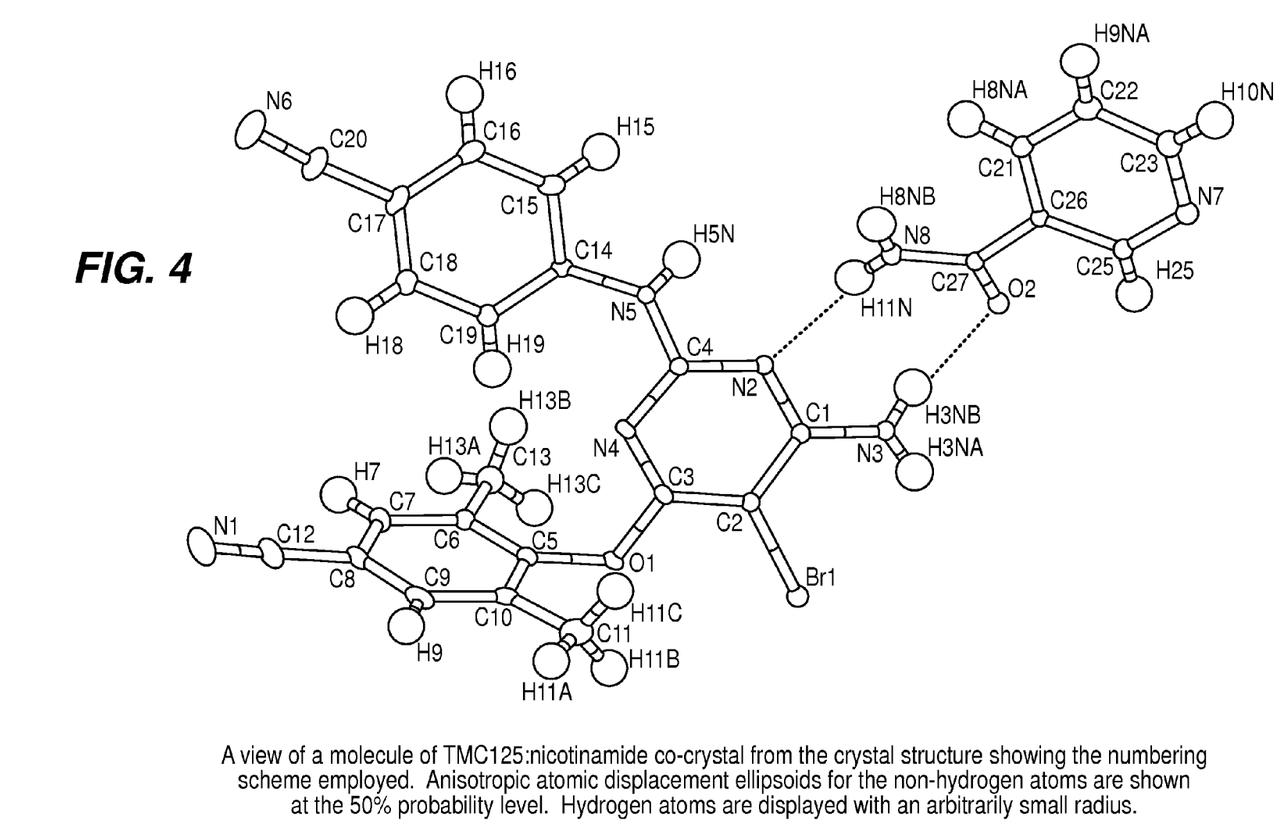
FIG. 4 shows a view of a molecule of TMC125:nicotinamide co-crystal from the crystal structure showing the numbering scheme employed.
Figure 5:
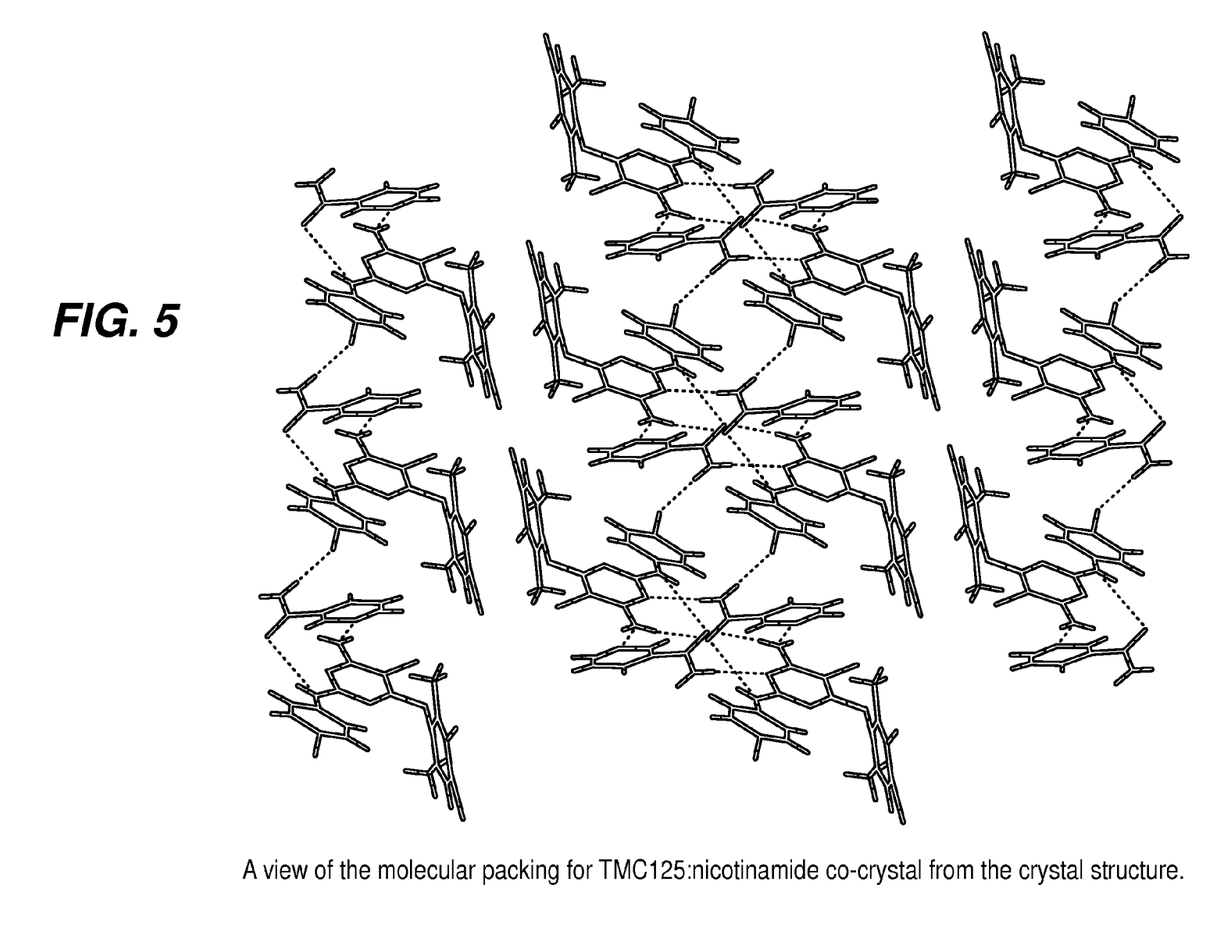
FIG. 5 shows a view of the molecular packing for TMC125:nicotinamide co-crystal from the crystal structure.

FIGS. 4-5 show the spacial arrangement of the co-crystal and the molecular packing in the crystal structure.

TABLE 1

Sample and crystal data for etravirine:nicotinamide.

| | |
|---|---|
| Identification code | TMC125:nicotinamide |
| Empirical formula | $C_{26}H_{21}BrN_8O_2$ |
| Formula weight | 557.42 |
| Temperature | 100(2) K |
| Wavelength | 0.71073 Å |
| Crystal size | 0.38 × 0.21 × 0.09 mm |
| Crystal habit | clear plate |
| Crystal system | Monoclinic |
| Space group | P2(1)/c |
| Unit cell dimensions | a = 8.1720(4) Å  α = 90° |
| | b = 9.0125(4) Å  β = 94.918(3)° |
| | c = 34.7072(14) Å  γ = 90° |
| Volume | 2546.8(2) Å$^3$ |
| Z | 4 |
| Density (calculated) | 1.454 Mg/m$^3$ |
| Absorption coefficient | 1.654 mm$^{-1}$ |
| F(000) | 1136 |

TABLE 2

Data collection and structure refinement for TMC125:nicotinamide.

| | |
|---|---|
| Diffractometer | CCD area detector |
| Radiation source | fine-focus sealed tube, MoKα |
| Generator power | 1.5 kW (50 kV, 30 mA) |
| Detector distance | 4.0 cm |
| Data collection method | phi and omega scans |
| Theta range for data collection | 2.34 to 36.89° |
| Index ranges | −13 ≤ h ≤ 13, −12 ≤ k ≤ 14, −57 ≤ l ≤ 56 |
| Reflections collected | 40173 |
| Independent reflections | 11331 [R(int) = 0.0356] |
| Coverage of independent reflections | 88.0% |
| Absorption correction | multi-scan |
| Max. and min. transmission | 0.8627 and 0.5721 |
| Structure solution technique | Patterson method |
| Structure solution program | SHELXS-97 (Sheldrick, 1990) |
| Refinement technique | Full-matrix least-squares on $F^2$ |
| Refinement program | SHELXL-97 (Sheldrick, 1997) |
| Function minimized | $\Sigma w(F_o^2 - F_c^2)^2$ |
| Data/restraints/parameters | 11331/0/418 |
| Goodness-of-fit on $F^2$ | 1.053 |
| $\Delta/\sigma_{max}$ | 0.006 |
| Final R indices | R1 = 0.0484, wR2 = 0.0969 |
| 8328 data; I > 2σ(I) | all data R1 = 0.0776, wR2 = 0.1070 |
| Weighting scheme | $w = 1/[\sigma^2(F_o^2) + [(0.0350P)^2 + 2.4661P]$ where $P = [MAX(F_o^2, 0) + 2F_c^2]/3$ |
| Friedel pairs | 7705 |
| Largest diff. peak and hole | 1.283 and −1.407 eÅ$^{-3}$ |
| R.M.S. deviation from the mean | 0.085 eÅ$^{-3}$ |

TABLE 3

Atomic coordinates and equivalent isotropic atomic displacement parameters (Å$^2$) for TMC125:nicotinamide. U(eq) is defined as one third of the trace of the orthogonalized $U_{ij}$ tensor.

| | x/a | y/b | z/c | U(eq) |
|---|---|---|---|---|
| Br1 | 0.35864(3) | −0.22963(2) | 0.827784(5) | 0.02659(6) |
| C1 | 0.35562(19) | −0.09399(17) | 0.90293(4) | 0.0144(3) |
| O1 | 0.14496(15) | 0.04327(13) | 0.81405(3) | 0.0182(2) |
| N1 | −0.4016(2) | 0.5763(2) | 0.75994(5) | 0.0350(4) |
| N2 | 0.31471(17) | 0.01342(15) | 0.92750(4) | 0.0147(2) |
| O2 | 0.51921(16) | 0.74577(13) | −0.00003(3) | 0.0190(2) |
| C2 | 0.2991(2) | −0.08558(18) | 0.86326(4) | 0.0164(3) |
| C3 | 0.20124(19) | 0.03378(17) | 0.85201(4) | 0.0149(3) |
| N3 | 0.4533(2) | −0.20263(16) | 0.91744(4) | 0.0199(3) |
| N4 | 0.15936(17) | 0.14090(15) | 0.87589(4) | 0.0150(2) |
| C4 | 0.22241(19) | 0.12488(17) | 0.91246(4) | 0.0138(3) |
| N5 | 0.19501(18) | 0.23362(16) | 0.93908(4) | 0.0173(3) |
| C5 | 0.0347(2) | 0.15726(18) | 0.80277(4) | 0.0149(3) |
| C6 | 0.0934(2) | 0.30091(18) | 0.79778(4) | 0.0159(3) |
| N6 | −0.0942(2) | 0.9355(2) | 0.93437(6) | 0.0355(4) |
| C7 | −0.0220(2) | 0.40903(19) | 0.78547(5) | 0.0178(3) |
| N7 | 0.43330(18) | 0.50238(16) | 0.09856(4) | 0.0186(3) |
| C8 | −0.1861(2) | 0.3705(2) | 0.77708(4) | 0.0180(3) |
| N8 | 0.3184(2) | 0.90817(17) | 0.01164(4) | 0.0195(3) |
| C9 | −0.2388(2) | 0.2247(2) | 0.78043(4) | 0.0193(3) |
| C10 | −0.1286(2) | 0.11542(19) | 0.79420(4) | 0.0163(3) |
| C11 | −0.1842(3) | −0.0406(2) | 0.80140(6) | 0.0259(4) |
| C12 | −0.3048(2) | 0.4851(2) | 0.76642(5) | 0.0247(4) |
| C13 | 0.2710(2) | 0.3406(2) | 0.80633(6) | 0.0228(3) |
| C14 | 0.13318(19) | 0.37648(17) | 0.93417(5) | 0.0156(3) |
| C15 | 0.1577(2) | 0.4694(2) | 0.96658(5) | 0.0227(3) |
| C16 | 0.0997(2) | 0.6130(2) | 0.96548(6) | 0.0244(4) |
| C17 | 0.0171(2) | 0.66767(19) | 0.93165(5) | 0.0208(3) |
| C18 | −0.0068(2) | 0.5769(2) | 0.89916(5) | 0.0239(4) |
| C19 | 0.0497(2) | 0.4317(2) | 0.90023(5) | 0.0212(3) |
| C20 | −0.0456(2) | 0.8161(2) | 0.93201(6) | 0.0257(4) |
| C21 | 0.3578(2) | 0.80433(19) | 0.09185(5) | 0.0192(3) |
| C22 | 0.3531(2) | 0.7309(2) | 0.12687(5) | 0.0245(3) |
| C23 | 0.3910(2) | 0.5813(2) | 0.12880(5) | 0.0204(3) |
| C25 | 0.4390(2) | 0.57437(18) | 0.06482(5) | 0.0169(3) |
| C26 | 0.40178(19) | 0.72393(18) | 0.06000(4) | 0.0150(3) |
| C27 | 0.4178(2) | 0.79452(17) | 0.02149(4) | 0.0155(3) |

TABLE 4

Bond lengths (Å) for TMC125:nicotinamide.

| | | | |
|---|---|---|---|
| Br1—C2 | 1.8817(16) | C1—N3 | 1.334(2) |
| C1—N2 | 1.351(2) | C1—C2 | 1.416(2) |
| O1—C3 | 1.3603(18) | O1—C5 | 1.4000(19) |
| N1—C12 | 1.150(2) | N2—C4 | 1.3352(19) |
| O2—C27 | 1.243(2) | C2—C3 | 1.377(2) |
| C3—N4 | 1.336(2) | N4—C4 | 1.3361(19) |
| C4—N5 | 1.378(2) | N5—C14 | 1.388(2) |
| C5—C10 | 1.394(2) | C5—C6 | 1.396(2) |
| C6—C7 | 1.397(2) | C6—C13 | 1.500(2) |
| N6—C20 | 1.153(2) | C7—C8 | 1.392(2) |
| N7—C23 | 1.337(2) | N7—C25 | 1.343(2) |
| C8—C9 | 1.391(3) | C8—C12 | 1.443(2) |
| N8—C27 | 1.333(2) | C9—C10 | 1.391(2) |
| C10—C11 | 1.505(3) | C14—C19 | 1.401(2) |
| C14—C15 | 1.403(2) | C15—C16 | 1.378(2) |
| C16—C17 | 1.393(3) | C17—C18 | 1.393(3) |
| C17—C20 | 1.433(2) | C18—C19 | 1.387(2) |
| C21—C22 | 1.387(2) | C21—C26 | 1.395(2) |
| C22—C23 | 1.384(3) | C25—C26 | 1.389(2) |
| C26—C27 | 1.496(2) | | |

Symmetry transformations used to generate equivalent atoms.

TABLE 5

Bond angles (°) for TMC125:nicotinamide.

| | | | |
|---|---|---|---|
| N3—C1—N2 | 117.40(13) | N3—C1—C2 | 122.73(14) |
| N2—C1—C2 | 119.84(14) | C3—O1—C5 | 118.24(12) |
| C4—N2—C1 | 117.04(13) | C3—C2—C1 | 116.78(14) |
| C3—C2—Br1 | 122.00(11) | C1—C2—Br1 | 121.22(11) |
| N4—C3—O1 | 118.17(13) | N4—C3—C2 | 124.20(13) |
| O1—C3—C2 | 117.63(14) | C3—N4—C4 | 114.39(13) |
| N2—C4—N4 | 127.69(14) | N2—C4—N5 | 113.07(13) |
| N4—C4—N5 | 119.23(13) | C4—N5—C14 | 130.97(13) |
| C10—C5—C6 | 123.85(14) | C10—C5—O1 | 116.26(14) |
| C6—C5—O1 | 119.69(14) | C5—C6—C7 | 117.03(15) |
| C5—C6—C13 | 122.23(15) | C7—C6—C13 | 120.71(16) |
| C8—C7—C6 | 120.21(16) | C23—N7—C25 | 117.25(15) |
| C7—C8—C9 | 121.17(15) | C7—C8—C12 | 119.34(17) |
| C9—C8—C12 | 119.44(16) | C10—C9—C8 | 120.10(15) |
| C9—C10—C5 | 117.49(15) | C9—C10—C11 | 121.49(16) |
| C5—C10—C11 | 120.96(16) | N1—C12—C8 | 176.3(2) |
| N5—C14—C19 | 125.34(14) | N5—C14—C15 | 115.44(14) |
| C19—C14—C15 | 119.21(15) | C16—C15—C14 | 120.88(16) |
| C15—C16—C17 | 119.74(16) | C18—C17—C16 | 119.92(16) |
| C18—C17—C20 | 122.01(17) | C16—C17—C20 | 118.05(17) |
| C19—C18—C17 | 120.60(16) | C18—C19—C14 | 119.65(16) |
| N6—C20—C17 | 176.4(2) | C22—C21—C26 | 118.37(16) |
| C23—C22—C21 | 118.96(16) | N7—C23—C22 | 123.51(16) |
| N7—C25—C26 | 123.39(15) | C25—C26—C21 | 118.52(15) |
| C25—C26—C27 | 119.04(14) | C21—C26—C27 | 122.38(14) |
| O2—C27—N8 | 122.72(15) | O2—C27—C26 | 120.03(14) |
| N8—C27—C26 | 117.24(14) | | |

Symmetry transformations used to generate equivalent atoms:

TABLE 6

Torsion angles (°) for TMC125:nicotinamide.

| | | | |
|---|---|---|---|
| N3—C1—N2—C4 | 177.37(16) | C2—C1—N2—C4 | −0.7(2) |
| N3—C1—C2—C3 | −178.92(17) | N2—C1—C2—C3 | −1.0(2) |
| N3—C1—C2—Br1 | 0.1(2) | N2—C1—C2—Br1 | 178.08(12) |
| C5—O1—C3—N4 | −5.6(2) | C5—O1—C3—C2 | 174.93(15) |
| C1—C2—C3—N4 | 0.9(3) | Br1—C2—C3—N4 | −178.11(13) |
| C1—C2—C3—O1 | −179.61(15) | Br1—C2—C3—O1 | 1.4(2) |
| O1—C3—N4—C4 | −178.67(14) | C2—C3—N4—C4 | 0.8(2) |
| C1—N2—C4—N4 | 2.8(3) | C1—N2—C4—N5 | −176.29(14) |
| C3—N4—C4—N2 | −2.8(3) | C3—N4—C4—N5 | 176.23(15) |
| N2—C4—N5—C14 | 166.77(17) | N4—C4—N5—C14 | −12.4(3) |
| C3—O1—C5—C10 | −106.03(16) | C3—O1—C5—C6 | 78.90(19) |
| C10—C5—C6—C7 | 3.6(2) | O1—C5—C6—C7 | 178.29(14) |
| C10—C5—C6—C13 | −178.31(16) | O1—C5—C6—C13 | −3.6(2) |
| C5—C6—C7—C8 | −2.8(2) | C13—C6—C7—C8 | 179.06(16) |
| C6—C7—C8—C9 | −0.5(2) | C6—C7—C8—C12 | 176.70(15) |
| C7—C8—C9—C10 | 3.2(2) | C12—C8—C9—C10 | −173.92(15) |
| C8—C9—C10—C5 | −2.5(2) | C8—C9—C10—C11 | 174.71(15) |
| C6—C5—C10—C9 | −1.0(2) | O1—C5—C10—C9 | −175.81(13) |
| C6—C5—C10—C11 | −178.19(15) | O1—C5—C10—C11 | 7.0(2) |
| C7—C8—C12—N1 | −98(4) | C9—C8—C12—N1 | 79(4) |
| C4—N5—C14—C19 | 15.1(3) | C4—N5—C14—C15 | −165.44(18) |
| N5—C14—C15—C16 | −179.01(18) | C19—C14—C15—C16 | 0.5(3) |
| C14—C15—C16—C17 | −0.7(3) | C15—C16—C17—C18 | 0.1(3) |
| C15—C16—C17—C20 | 178.20(18) | C16—C17—C18—C19 | 0.6(3) |
| C20—C17—C18—C19 | −177.40(18) | C17—C18—C19—C14 | −0.7(3) |
| N5—C14—C19—C18 | 179.67(18) | C15—C14—C19—C18 | 0.2(3) |
| C18—C17—C20—N6 | 167(3) | C16—C17—C20—N6 | −11(3) |
| C26—C21—C22—C23 | −0.4(3) | C25—N7—C23—C22 | 0.2(3) |
| C21—C22—C23—N7 | 0.4(3) | C23—N7—C25—C26 | −0.7(3) |
| N7—C25—C26—C21 | 0.7(3) | N7—C25—C26—C27 | 177.85(15) |
| C22—C21—C26—C25 | −0.1(3) | C22—C21—C26—C27 | −177.17(16) |
| C25—C26—C27—O2 | −28.7(2) | C21—C26—C27—O2 | 148.41(16) |
| C25—C26—C27—N8 | 150.50(16) | C21—C26—C27—N8 | −32.4(2) |

Symmetry transformations used to generate equivalent atoms.

TABLE 7

Anisotropic atomic displacement parameters (Å$^2$) for TMC125:nicotinamide.
The anisotropic atomic displacement factor exponent takes the form:
$$-2\pi^2 [h^2 a^{*2} U_{11} + \ldots + 2hka^* b^* U_{12}]$$

|     | $U_{11}$ | $U_{22}$ | $U_{33}$ | $U_{23}$ | $U_{13}$ | $U_{12}$ |
|-----|----------|----------|----------|----------|----------|----------|
| Br1 | 0.04665(12) | 0.01861(8) | 0.01341(7) | −0.00438(6) | −0.00368(6) | 0.01501(7) |
| C1  | 0.0190(7)  | 0.0117(6)  | 0.0120(6)  | 0.0001(5)   | −0.0022(5)  | 0.0019(5)  |
| O1  | 0.0265(6)  | 0.0163(5)  | 0.0105(5)  | −0.0016(4)  | −0.0054(4)  | 0.0075(4)  |
| N1  | 0.0300(9)  | 0.0432(11) | 0.0316(9)  | 0.0122(8)   | 0.0020(7)   | 0.0152(8)  |
| N2  | 0.0204(6)  | 0.0122(6)  | 0.0109(5)  | −0.0009(4)  | −0.0023(4)  | 0.0040(5)  |
| O2  | 0.0261(6)  | 0.0184(6)  | 0.0122(4)  | −0.0001(4)  | −0.0004(4)  | 0.0082(4)  |
| C2  | 0.0244(8)  | 0.0123(6)  | 0.0119(6)  | −0.0017(5)  | −0.0017(5)  | 0.0047(5)  |
| C3  | 0.0190(7)  | 0.0139(7)  | 0.0109(6)  | −0.0002(5)  | −0.0040(5)  | 0.0012(5)  |
| N3  | 0.0319(8)  | 0.0144(7)  | 0.0125(6)  | −0.0004(5)  | −0.0029(5)  | 0.0102(5)  |
| N4  | 0.0200(6)  | 0.0134(6)  | 0.0109(5)  | −0.0008(4)  | −0.0029(4)  | 0.0037(5)  |
| C4  | 0.0169(7)  | 0.0118(6)  | 0.0122(6)  | −0.0012(5)  | −0.0019(5)  | 0.0025(5)  |
| N5  | 0.0248(7)  | 0.0139(6)  | 0.0121(5)  | −0.0024(5)  | −0.0040(5)  | 0.0069(5)  |
| C5  | 0.0194(7)  | 0.0152(7)  | 0.0097(6)  | 0.0002(5)   | −0.0014(5)  | 0.0029(5)  |
| C6  | 0.0163(7)  | 0.0168(7)  | 0.0142(6)  | 0.0009(5)   | −0.0013(5)  | 0.0014(5)  |
| N6  | 0.0301(9)  | 0.0215(8)  | 0.0561(12) | −0.0013(8)  | 0.0098(8)   | 0.0097(7)  |
| C7  | 0.0206(8)  | 0.0171(7)  | 0.0157(6)  | 0.0037(5)   | 0.0016(6)   | 0.0031(6)  |
| N7  | 0.0230(7)  | 0.0167(6)  | 0.0161(6)  | 0.0013(5)   | 0.0013(5)   | 0.0037(5)  |
| C8  | 0.0186(7)  | 0.0248(8)  | 0.0105(6)  | 0.0037(5)   | 0.0006(5)   | 0.0066(6)  |
| N8  | 0.0264(7)  | 0.0159(7)  | 0.0159(6)  | 0.0017(5)   | 0.0002(5)   | 0.0080(5)  |
| C9  | 0.0171(7)  | 0.0285(8)  | 0.0121(6)  | −0.0008(6)  | −0.0003(5)  | −0.0004(6) |
| C10 | 0.0197(7)  | 0.0203(7)  | 0.0088(6)  | −0.0008(5)  | 0.0006(5)   | −0.0021(6) |
| C11 | 0.0324(10) | 0.0224(9)  | 0.0229(8)  | −0.0009(7)  | 0.0032(7)   | −0.0080(7) |
| C12 | 0.0226(8)  | 0.0345(10) | 0.0172(7)  | 0.0074(7)   | 0.0021(6)   | 0.0073(7)  |
| C13 | 0.0168(8)  | 0.0220(9)  | 0.0289(9)  | −0.0007(7)  | −0.0013(6)  | 0.0000(6)  |
| C14 | 0.0172(7)  | 0.0123(6)  | 0.0170(6)  | −0.0028(5)  | −0.0013(5)  | 0.0034(5)  |
| C15 | 0.0260(9)  | 0.0190(8)  | 0.0218(8)  | −0.0072(6)  | −0.0059(6)  | 0.0071(6)  |
| C16 | 0.0243(9)  | 0.0183(8)  | 0.0296(9)  | −0.0098(7)  | −0.0040(7)  | 0.0046(6)  |
| C17 | 0.0174(7)  | 0.0136(7)  | 0.0317(9)  | −0.0016(6)  | 0.0033(6)   | 0.0048(5)  |
| C18 | 0.0274(9)  | 0.0190(8)  | 0.0247(8)  | 0.0009(6)   | −0.0014(7)  | 0.0107(6)  |
| C19 | 0.0269(9)  | 0.0180(8)  | 0.0176(7)  | −0.0023(6)  | −0.0041(6)  | 0.0093(6)  |
| C20 | 0.0192(8)  | 0.0184(8)  | 0.0400(10) | −0.0008(7)  | 0.0054(7)   | 0.0048(6)  |
| C21 | 0.0246(8)  | 0.0157(7)  | 0.0172(7)  | −0.0020(5)  | 0.0016(6)   | 0.0070(6)  |
| C22 | 0.0329(9)  | 0.0249(9)  | 0.0164(7)  | −0.0025(6)  | 0.0064(6)   | 0.0092(7)  |
| C23 | 0.0237(8)  | 0.0228(8)  | 0.0152(7)  | 0.0023(6)   | 0.0047(6)   | 0.0037(6)  |
| C25 | 0.0225(8)  | 0.0146(7)  | 0.0133(6)  | −0.0009(5)  | 0.0004(5)   | 0.0053(5)  |
| C26 | 0.0180(7)  | 0.0142(6)  | 0.0124(6)  | −0.0007(5)  | −0.0008(5)  | 0.0041(5)  |
| C27 | 0.0209(7)  | 0.0118(7)  | 0.0132(6)  | −0.0014(5)  | −0.0029(5)  | 0.0031(5)  |

TABLE 8

Hydrogen atom coordinates and isotropic atomic displacement parameters (Å$^2$) for TMC125:nicotinamide.

|       | x/a | y/b | z/c | U |
|-------|-----|-----|-----|---|
| H3NA  | 0.475(3) | −0.280(3) | 0.9045(7) | 0.020(5) |
| H3NB  | 0.481(3) | −0.202(3) | 0.9414(8) | 0.031(6) |
| H5N   | 0.249(3) | 0.221(3)  | 0.9594(7) | 0.026(6) |
| H7    | 0.012(3) | 0.504(3)  | 0.7824(6) | 0.023(6) |
| H11N  | 0.323(3) | 0.948(3)  | −0.0097(8)| 0.035(7) |
| H8NB  | 0.252(3) | 0.941(3)  | 0.0269(7) | 0.027(6) |
| H9    | −0.349(3)| 0.196(3)  | 0.7732(6) | 0.019(5) |
| H11C  | −0.166(3)| −0.062(3) | 0.8288(8) | 0.047(8) |
| H11B  | −0.123(4)| −0.109(3) | 0.7880(8) | 0.049(8) |
| H11A  | −0.296(4)| −0.052(3) | 0.7915(9) | 0.050(8) |
| H13A  | 0.303(3) | 0.426(3)  | 0.7926(8) | 0.039(7) |
| H13B  | 0.293(3) | 0.362(3)  | 0.8330(8) | 0.042(7) |
| H13C  | 0.342(4) | 0.263(3)  | 0.7991(8) | 0.043(8) |
| H15   | 0.216(3) | 0.435(3)  | 0.9897(7) | 0.030(6) |
| H16   | 0.114(3) | 0.676(3)  | 0.9882(7) | 0.033(6) |
| H18   | −0.065(3)| 0.614(3)  | 0.8745(7) | 0.034(7) |
| H19   | 0.033(3) | 0.374(3)  | 0.8787(8) | 0.036(7) |
| H8NA  | 0.333(3) | 0.909(3)  | 0.0910(7) | 0.027(6) |
| H9NA  | 0.326(3) | 0.779(3)  | 0.1487(7) | 0.029(6) |
| H10N  | 0.389(3) | 0.527(2)  | 0.1518(6) | 0.018(5) |
| H25   | 0.469(3) | 0.523(3)  | 0.0446(6) | 0.021(5) |

TABLE 9

Selected hydrogen bond information for TMC125:nicotinamide.
(Å and °).

| D-H...A | d(D-H) | d(H...A) | d(D...A) | <(DHA) |
|---------|--------|----------|----------|--------|
| N8—H11N...N2#1  | 0.83(3) | 2.25(3) | 3.068(2)   | 169(3) |
| N3—H3NA...N7#2  | 0.85(2) | 2.15(2) | 2.925(2)   | 151(2) |
| N3—H3NB...O2#3  | 0.84(3) | 2.08(3) | 2.9063(18) | 165(2) |
| N5—H5N...O2#4   | 0.81(3) | 2.28(2) | 3.0194(19) | 152(2) |
| N8—H8NB...N6#5  | 0.84(3) | 2.24(3) | 3.072(2)   | 170(2) |

Symmetry transformations used to generate equivalent atoms:
1 x, y + 1, z − 1
2 −x + 1, −y, −z + 1
3 x, y − 1, z + 1
4 −x + 1, −y + 1, −z + 1
5 −x, −y + 2, −z + 1

Example 3

Dissolution Experiments with
TMC125/Nicotinamide Co-Crystal

This dissolution experiment was focused on looking at the difference between the cocrystal and TMC125 free base both neat and mixed with HPMC E5 Cps.

The loadings were:

A: 100 mg co-crystal: 100 mg HPMC E5 Cps (powder blend)
B: 100 mg co-crystal (powder)
C: 78 mg free base: 100 mg HPMC E5 Cps (powder blend)
D: 78 mg free base (powder)

Powders were dispensed to 20 mL vials and in 20 mL of 10 mM HCl with 1% TPGS (d-alpha-tocopheryl polyethylene glycol 1000 succinate) was added to each vial. Each vial was stirred at 500 rpm via stir bar at 37° C. and 500 µL aliquots were taken at 5, 10, 20, 40, and 60 minutes, filtered through a 0.45 µm nylon filter via centrifugation and the solute was diluted in half and analyzed by HPLC for the concentration of TMC125.

The results are listed in the following table.

| | Concentration of TMC125 (µg/mL) (Simulated Gastric Fluid with 1% TPGS) | | | |
|---|---|---|---|---|
| Time (min) | 1:1 Co-cryst.:HPMC E5Cps | Neat Co-cryst | 1:1 TMC125 FB:HPMC E5 | Neat TMC125 FB |
| 5 | 374.65 | 301.59 | 47.00 | 22.36 |
| 10 | 589.76 | 167.03 | 30.41 | 52.04 |
| 20 | 719.76 | 112.92 | 39.35 | 57.03 |
| 30 | 748.78 | 97.98 | 43.78 | 58.96 |
| 45 | 657.07 | 83.07 | 45.07 | 59.83 |
| 60 | 539.53 | 79.72 | 47.14 | 60.10 |

FB: free base
Co-cryst.: co-crystal of TMC125 and nicotinamide as prepared in example 1.

Figure 7:
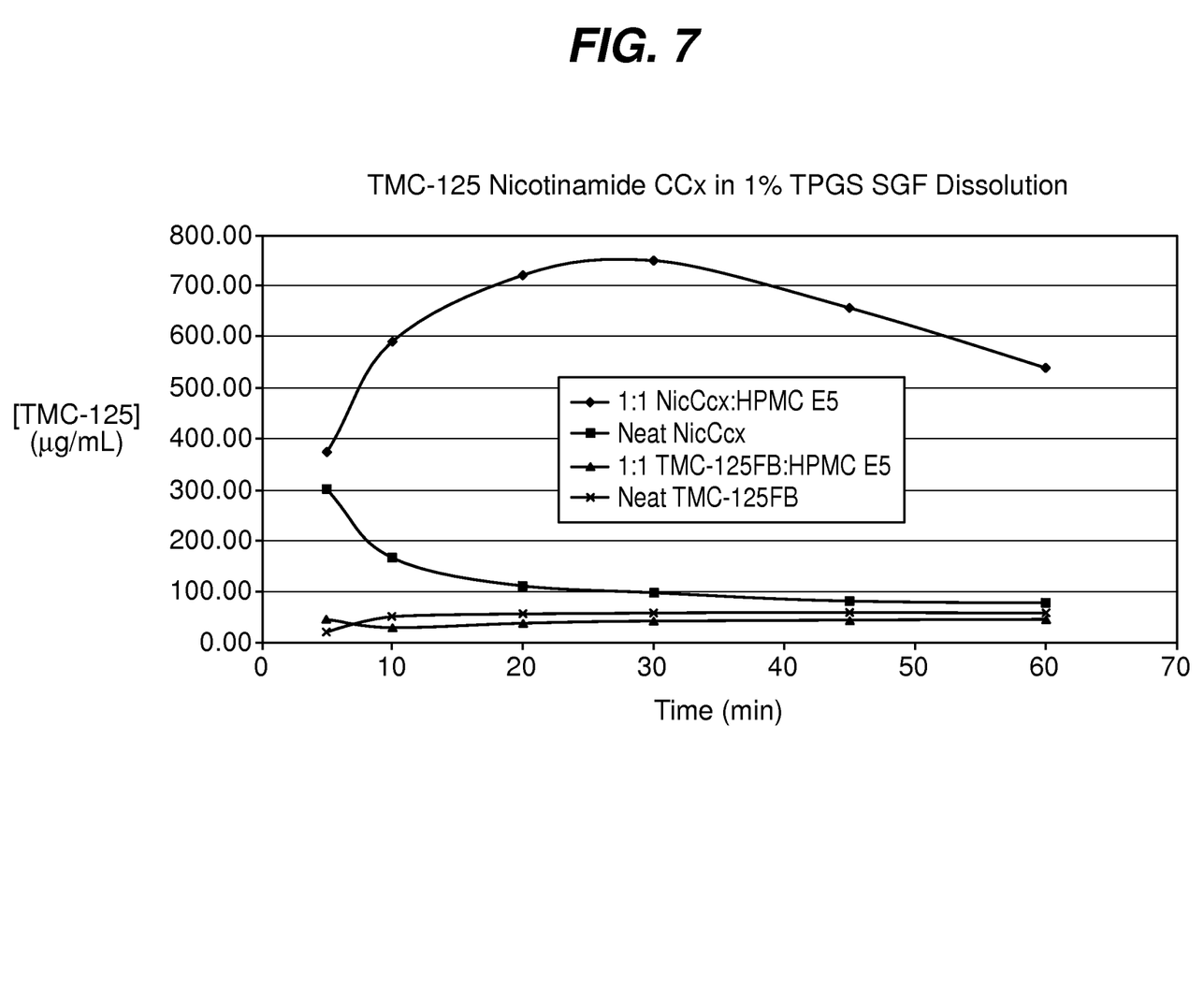
FIG. 7 shows a plot for the results from Example 3, dissolution experiments with TMC125:nicotinamide co-crystal.

The results are plotted in FIG. 7.

Example 4

Compositions

| | |
|---|---|
| Co-crystals of TMC125 and nicotinamide | 256 mg |
| Silicified microcrystalline cellulose | 225.28 mg |
| Crospovidone K64 | 9.85 mg |
| Mg stearate | 1.15 mg |
| Opadry ™ | 19.16 mg |
| Co-crystals of TMC125 and nicotinamide | 256 mg |
| HPMC 2910 E5 | 256 mg |
| Silicified microcrystalline cellulose | 225.28 mg |
| Crospovidone K64 | 9.85 mg |
| Mg stearate | 1.15 mg |
| Opadry ™ | 19.16 mg |
| Co-crystals of TMC125 and nicotinamide | 256 mg |
| HPMC 2910 E5 | 128 mg |
| Nicotinamide | 256 mg |
| Silicified microcrystalline cellulose | 225.28 mg |
| Crospovidone K64 | 9.85 mg |
| Mg stearate | 1.15 mg |
| Opadry ™ | 19.16 mg |
| Co-crystals of TMC125 and nicotinamide | 256 mg |
| HPMC 2910 E5 | 128 mg |
| Nicotinamide | 256 mg |
| PVP | 256 mg |
| Silicified microcrystalline cellulose | 225.28 mg |
| Crospovidone K64 | 9.85 mg |
| Mg stearate | 1.15 mg |
| Opadry ™ | 19.16 mg |

The above mentioned ingredients are mixed and processed into tablets using standard methodologies.

The invention claimed is:

1. Co-crystal of etravirine and nicotinamide.

2. The co-crystal of claim 1, wherein the etravirine and nicotinamide are present in a 1:1 molar ratio.

3. A process for preparing the co-crystal of claim 1 or 2, said process comprising dissolving etravirine and nicotinamide in a halogenated hydrocarbon solvent or a polar, aprotic solvent, if desired by warming the mixture to complete dissolution; removing the solvent, to provoke crystallization, by evaporation; and allowing the mixture to cool to room temperature whereupon the co-crystal precipitates.

4. The process of claim 3, wherein etravirine is dissolved in a halogenated hydrocarbon solvent or a polar, aprotic solvent whereupon nicotinamide is added; the whole is warmed until complete dissolution; solvent is removed by evaporation by a stream of inert gas while allowing the mixture to cool to room temperature; the co-crystal that is formed is filtered off and optionally washed and dried.

5. The process of claim 3, wherein the solvent is removed by introducing a stream of inert gas.

6. A pharmaceutical composition comprising an anti-HIV effective amount of the etravirine and nicotinamide co-crystal defined in claims 1 or claim 2, and a carrier.

7. A composition comprising the etravirine and nicotinamide co-crystal as defined in claim 1 or claim 2, and further comprising one or more dissolution improving ingredients selected from hydroxypropyl methylcellulose (HPMC), hydroxypropylmethylcellulose phthalate (HPMCP), polyvinylpyrrolidone (PVP), a copolymer of vinylpyrrolidone and vinyl acetate (PVPcoVA), and nicotinamide, including mixtures thereof.

8. The composition of claim 7 wherein the weight/weight ratio between the etravirine and nicotinamide co-crystal and the total amount of the one or more dissolution improving ingredients is 1:1.

9. The composition of claim 7 wherein the one or more dissolution improving ingredients are selected from HPMC, PVP and nicotinamide.

10. The composition of claim 7, wherein the composition comprises the etravirine and nicotinamide co-crystal as defined in claim 1 or claim 2, and the dissolution improving ingredients PVP, nicotinamide and HPMC, in a 1:1:1:1/2 weight/weight ratio.

11. The composition of claim 7, wherein the HPMC is HPMC 2910 E5.

12. A pharmaceutical composition comprising the composition of claim 7 and a carrier.

13. A method for the treatment of HIV in a subject, said method comprising administration of co-crystal of claim 1 or claim 2 to the subject.

14. The composition of claim 8, wherein the composition comprises the etravirine and nicotinamide co-crystal as defined in claim 1 or claim 2, and the dissolution improving ingredients PVP, nicotinamide and HPMC, in a 1:1:1:1/2 weight/weight ratio.

15. The composition of claim 9, wherein the composition comprises the etravirine and nicotinamide co-crystal as defined in claim 1 or claim 2, and the dissolution improving ingredients PVP, nicotinamide and HPMC, in a 1:1:1:1/2 weight/weight ratio.

16. The composition of claim 8 wherein the one or more dissolution improving ingredients are selected from HPMC, PVP and nicotinamide.

17. The composition of claim 8, wherein the HPMC is HPMC 2910 E5.

18. The composition of claim 9, wherein the HPMC is HPMC 2910 E5.

19. A pharmaceutical composition comprising the composition of claim 8 and a carrier.

20. A pharmaceutical composition comprising the composition of claim 9 and a carrier.

21. A pharmaceutical composition comprising the composition of claim 10 and a carrier.

22. The process of claim 4, wherein the solvent is removed by introducing a stream of inert gas.

* * * * *